(12) United States Patent
Jenkins et al.

(10) Patent No.: US 6,423,550 B1
(45) Date of Patent: Jul. 23, 2002

(54) HOME ORAL FLUID SAMPLE COLLECTION DEVICE AND PACKAGE FOR MAILING OF SUCH DEVICE

(75) Inventors: Richard Jenkins, Kenneth Square, PA (US); James Phillip Galvin, Wilmington, DE (US); Helen Schneider, Florham Park; Richard L. Egan, Flemington, both of NJ (US)

(73) Assignee: Ortho Pharmaceutical Corporation, Raritan, NJ (US)

( * ) Notice: Subject to any disclaimer, the term of this patent is extended or adjusted under 35 U.S.C. 154(b) by 0 days.

(21) Appl. No.: 08/413,294

(22) Filed: Mar. 30, 1995

(51) Int. Cl.$^7$ ............................................. G01N 33/543
(52) U.S. Cl. ...................................................... 436/518
(58) Field of Search ................................ 435/291, 292, 435/294, 295; 422/55, 56, 57, 58, 61; 604/1; 128/760

(56) References Cited

U.S. PATENT DOCUMENTS

| | | | |
|---|---|---|---|
| 3,776,220 A | | 12/1973 | Monaghan |
| 3,915,806 A | | 10/1975 | Horlach |
| 4,387,725 A | * | 6/1983 | Mull ........................... 128/759 |
| 5,022,409 A | | 6/1991 | Goldstein et al. |
| 5,103,836 A | | 4/1992 | Goldstein et al. |
| 5,232,914 A | | 8/1993 | Fellman |
| 5,234,001 A | | 8/1993 | Goldstein et al. |
| 5,260,031 A | | 11/1993 | Seymour |
| 5,447,837 A | * | 9/1995 | Urnovitz ........................ 435/5 |

FOREIGN PATENT DOCUMENTS

| | | | |
|---|---|---|---|
| DE | 1 357 232 | 6/1974 | .......... G01N/21/00 |
| DE | 36 32 303 A1 | 4/1987 | .......... A61B/10/00 |
| EP | 0 155 747 A1 | 9/1985 | ............ C12M/1/30 |
| WO | WO 94/04078 | 3/1994 | .......... A61B/10/00 |

OTHER PUBLICATIONS

Webster's Dictionary, 1984.*

* cited by examiner

Primary Examiner—Bao-Thuy L. Nguyen
(74) Attorney, Agent, or Firm—Paul A. Coletti (57) ABSTRACT

This reagent strip is comprised of a testing portion which contains an absorbent cotton pad. This absorbent cotton pad may be placed in the mouth on the tongue to collect an oral fluid sample. A plastic frame surrounds the pad to help hold the fluid thereon. This testing strip contains at its opposite end a sealing mechanism for sealing engagement with a preservative pouch, and an oversized handle with a patient identifying mechanism. The preservative pouch of the present invention contains a pair of seals. The first seal, located proximally to the user, enables a preservative which is maintained within the pouch to be sealed during shipment of the pouch to the user. Thereafter, the user punctures the first seal upon placement of the reagent pad into the pouch. The sealing mechanism contained on the reagent pad then seals at the opening in the pouch to maintain the reagent pad in sealing arrangement within the pouch. At its distal end, the pouch contains a second sealing mechanism. This sealing mechanism helps protect the preservative as well as the oral sample, within the pouch during shipment from the user back to the testing laboratory.

14 Claims, 8 Drawing Sheets

HOME ORAL FLUID SAMPLE COLLECTION DEVICE AND PACKAGE FOR MAILING OF SUCH DEVICE

BACKGROUND OF THE INVENTION

Generally, this invention relates to a device useful for a patient to collect a sample of oral fluid for purposes of mailing the sample to a testing laboratory for various diagnostic measurement and testing of the patient's oral fluid, thereby indicating the presence of conditions such as infectious diseases in the individual. More specifically, the present invention relates to a sample collection device which a person can place in their mouth to collect an oral fluid sample. This oral collection device is then placed within a sealing pouch and then in a mailer and sent to a testing laboratory.

BACKGROUND OF THE INVENTION

It has been well-known that oral fluid samples may contain antibodies or antigens to various diseases, such as sexually transmitted diseases, for example human immuno deficiency virus (HIV). Further, other diseases and other states may also be tested in a patients oral fluid: Hepatitis B; Rubella; cytomegalovirus (CMV); hepatitis C virus (HCV); Toxoplasmosis; hepatitis A virus (HAV); Lyme Disease; testing for drug abuse; therapeutic drug monitoring; or DNA diagnostics.

Heretofore, it has been a known practice to take oral samples from a patient at a laboratory in order to determine the presence of such analytes. However, it has become desirable to be able to have the patient take a sample at home, and then send it in the mail to a testing service. The service then analyzes the sample in the laboratory and reports the result in confidence to the patient.

The collection of oral fluid samples from outside of a laboratory and then mailing them to a testing service presents its own difficulties. For instance, the sampling device must be reliable. It must be able to be preserved. It must be sealable within a device so that the sample does not leak or get contaminated during mailing. The sealing mechanism must be impermeable so that the sealing mechanism itself cannot be punctured during mailing. And, as an overriding concern, all of these functions must take place in a device which is small enough to incur low mailing costs while meeting postal regulations. Thus far, it has been unknown in the industry to provide for such a device.

Furthermore, once the device arrives at the testing laboratory, it is then desirable to recover the sample from the strip (e.g., by centrifugation). It may be desirable to keep the sample within the original pouch in which the sample has been mailed (to maintain sample identification and also to allows taking multiple testing in various analytical procedures), so that once again the sample is not in any way compromised. Therefore, it is desirable to have a mechanism which is capable of centrifugation within its own mailer.

SUMMARY OF THE INVENTION

The invention described herein provides for such concerns. There is disclosed a sample collection device which is comprised of a collection portion in the form of an absorbent cotton pad. This absorbent cotton pad may be placed in the mouth (generally on the tongue, although other locations may be acceptable) to collect an oral fluid sample. A plastic frame surrounds the pad to help hold the fluid collected thereon and maintain pad integrity. The handle of the device incorporates a sealing mechanism for sealing engagement with the collar of the preservative pouch. A barcode label is placed on the oversized handle as a patient identifying mechanism.

A narrow extension of the pad will continue up the central, hollow stem of the handle. A window is placed in the neck of the stick and a chemical is coated on the pad underneath the window, the chemical being chosen so that it will change color when sufficient oral fluid has been taken up by the pad. Various schemes have been devised for effecting the color change. The product is designed so that a consumer with no medical training will be able to easily and safely collect an oral fluid sample, know when there is a sufficiently collected sample, preserve the sample so that it survive shipment to the laboratory and receive information about HIV serotatus or other disease or drug in a completely confidential manner.

The preservative pouch of the present invention contains a pair of seals. The first seal, located proximally to the user, enables a preservative which is maintained within the pouch to be sealed during shipment of the pouch to the user. Thereafter, the user punctures the first seal upon placement of the reagent pad into the pouch. The sealing mechanism contained on the reagent pad then seals at the opening in the pouch to maintain the reagent pad in sealing arrangement within the pouch.

At its distal end, the pouch contains a second sealing mechanism, whose use will be further explained below. However, it is to be understood that this sealing mechanism helps protect the preservative as well as the oral sample, within the pouch during shipment from the user back to the testing laboratory.

Both the flexible pouch and the pad contained in sealing arrangement are inserted together into a mailing pouch. The mailing pouch is arranged so that the preservative pouch is not able to be punctured during mailing. This preservative pouch furthermore contains a latching mechanism so that the reagent strip and preservative pouch can be latched within the mailing pouch to be placed within a mailer and returned to the testing laboratory. This mailing pouch further contains a cuvette which is able to be punctured in the laboratory to obtain a portion of the sample of oral fluid collected after such original sample is centrifuged in its original pouch.

In use, the mechanism of the present invention is placed in the mail with the reagent pad holding collected oral sample within the pouch. This combination is placed into the mailing pouch and sent to the laboratory in a first class postage mailer. When at the laboratory, the technician can puncture the cuvette so that the user can take a separate sample of the sample already collected. To do so, the laboratory technician cuts away a portion of the mailing pouch, and places the remaining mailing pouch with the preservative pouch intact within a centrifuge. Or, the technician can remove the preservative pouch and reagent pad and thereafter place it within a centrifuge.

The preservative pouch contains the heretofore mentioned second distal seal. This seal is now broken during centrifugation. At this point, the oral sample which has been preserved through mailing is collected by within the mailing pouch and can be used to determine presence of various antibodies in any of a series well-known tests for the existence of such antibodies or other analytes.

BRIEF DESCRIPTION OF THE DRAWINGS

The present invention will be better understood in combination with the attached Figures in which.

DETAILED DESCRIPTION

By way of further description, those skilled in the art will understand the invention from the following:

(a) Sample Collection Device

The oral fluid sample is collected on a soft cotton pad which is held in a flexible plastic frame. The holder is flexible so that it will be comfortable for the user when it is held in the mouth. Positioning in the mouth is not critical, but for example, the pad may be placed comfortably on the tongue ensuring it is bathed by oral fluid in the patient's mouth. The pad will be made of medical grade 100% pure cotton. It will have no chemicals added to it. It will collect a representative sample of the oral fluid in the subject patient's mouth by being placed in the mouth, generally on the tongue ensuring it is bathed by oral fluid in the patient's mouth. The size and capacity of the pad is designed so that the color indicator (described below) changes color only when sufficient oral fluid (0.75 ml to 1.2 ml) has been absorbed by the pad as is required for the analytical procedures.

Main features of the Collection Device are:

Formed of a rectangular plastic frame which holds the absorbent pad. The pad is made of pure 100% cotton, either Whatman #427 or S.&S. #300. It will hold between 0.75 ml and 1.2 ml of the oral fluid sample.

There are no chemicals or flavors added to the pad. The pad is designed to collect a representative sample of the subject's oral fluid.

The frame has a hollow handle which holds a narrow extension of the pad.

Near the end of the handle is a clear plastic window for viewing the color change by the oral fluid of a dye prearranged on the cotton pad which indicates sufficient sample has been collected.

The end of the handle is designed to fit into a collar of the pouch so that once the end has been inserted into the collar, it cannot be easily removed. It also forms a leak-proof seal in the collar of the pouch. In one embodiment, the collar is larger than the mouth of a centrifuge tube, such that the pad will be prevented from falling to the bottom of the tube during centrifugation and reabsorbing the eluted sample.

(b) Adequate Sample Indicator

A narrow extension of the pad will continue up the central, hollow stem of the handle. A window is placed in the neck of the stick and a chemical dye is coated on the pad underneath the window and just outside the window, the chemical dye being chosen so that it will change color when sufficient oral fluid has been taken up by the pad. Various schemes have been devised for effecting the color change.

pH indicators

In one example, a pH indicator, in useful amounts of either Alizarin Red (AR), Bromocresol Purple (BP) or Bromocresol Green (BG), will be spotted on the pad material so that the indicator is visible through the window in the plastic stem. Initially, the indicator will be yellow or orange. When an adequate oral fluid sample has been collected, the indicator will turn to a dark red or purple color (with AR), or to a dark blue (with BP or BG).

Binding of stains by a protein

Another method of causing a color change will be to coat a colorless protein under the window area. Lower down on the neck of the pad a protein staining agent (which may be colored or colorless) will be coated. The oral fluid will transport the staining compound to the protein and cause the area under the window to become colored. An example would be to coat any dye such as Commasie Blue™ or an FDA approved water soluble dye as the stain and BSA (Bovine Serum Albumin) as the colorless protein.

It is also possible to combine some of these methods, e.g., a very soluble pH indicator may be coated below the window and a capture protein coated in the window area. The oral fluid will both cause a color change in the indicator and also carry it to the window area where it will be captured by the invisible protein. In this way, the color will go from colorless to blue, for example if either BP or BG is used.

By any of these techniques, the user will know when sufficient sample has been collected.

(c) Sample I.D. System

A unique number and/or bar code will be printed onto the back of the collection stick, or on the handle or attached to a separable label on the handle, with a matching identifier held by the user. The same number will be printed on the card which the user will retain. The card will be attached to the stick and will be removed by the user before taking an oral sample.

(d) The Preservative and its Container

The preservative will be held in a flexible, impermeable plastic pouch with a series of temporary seals. At the top of the pouch is a plastic collar. The collar and the top of the collection stick are designed so that they have complimentary ridges molded into their matching surfaces. This feature results in a tight fit between the top of the collection stick and the collar to prevent spillage during transit to the lab, and also to prevent the user from removing the holder from the pouch.

The main features of the preservative and pouch are as follows:

The upper temporary seal breaks when the user inserts the sample collection device into the pouch. After breaking the seal, the holder and pad enter into the preservative solution so that the pad is bathed with preservative which will stabilize the sample until it reaches the lab.

The lower temporary seal is designed to be sufficiently strong so as to survive handling and shipping to the lab, but weak enough to break under centrifugal force when the pouch plus pad holder assembly is centrifuged at the lab.

The pouch will be surrounded by a leak-free rigid or semi-rigid container which will also be built into the plastic protector for the sample. On receipt of the mailer containing the sample at the laboratory, either the whole mailer will be centrifuged, such that after centrifugation, the sample collects in the bottom of the plastic protection device (FIG. 14), or the leak-proof container will be automatically extracted from the mailer and centrifuged. The container will receive the eluate of sample plus preservative from the pad during centrifugation.

The preservative will contain an approved food coloring, so that the total volume of the recovered eluate can be easily determined either visually or by an instrument to ensure that the sample is adequate. A channel or orifice will be provided so that aliquots of the eluate can be withdrawn for the various analytical procedures. This leak-proof container will be used to hold the sample during storage at the lab. This will greatly reduce the chances for sample contamination or sample mix-up because the sample will always be in its original container with the patient I.D. and bar code still present.

The composition of the preservative will be an aqueous solution, containing the following ingredients in PBS (Phosphate Buffered Saline):
0.05 to 0.5% Bronidox®
0.05 to 0.5% Gentamicin Sulfate
0.05 to 0.5% Aprotenin
0.05 to 0.5% Tween 20

A small concentration of an approved food coloring can also be added.

(e) The Mailer for return of the sample

The pouch holding the preservative will be mounted directly in the return mailer provided to the customer.

The main features of the mailer are as follows:

The mailer will be made of a strong, flexible material (e.g. cardboard or Tyvek®). Inside will be a strong, thin, flexible plastic or cardboard sheath, which will protect the pouch from puncture during shipment.

The pouch will be firmly attached to the sheath so that the pouch is inside the sheath and the plastic collar of the pouch is flush with the top of the sheath.

After collecting an adequate sample, the user inserts the pad holder into the pouch and pushes until the top of the holder snaps firmly into the collar of the pouch. The mailer is sealed by removing the cover from a self-adhesive patch on the folding cover, and folding over the flap.

The pouch is held inside the leak-proof container. This container is attached to the protective sheath in such a way that it can easily be removed from the mailer on receipt at the lab, e.g., by having a perforated area of the sheath surrounding the point of attachment of the leak proof container to the larger plastic sheath or frame.

The mailer/pouch combination is designed so that it meets all U.S. postal regulations (especially size, weight, thickness (no more than ¼") in thickness and flexibility) so that it is accepted at the first class letter rate, and hence can be returned to the lab as fast and at as low a cost as possible.

(f) Analysis of the Sample

Upon receipt at the reference lab, either the entire mailer is centrifuged or the leak-proof container, including the pouch and collection stick, will be removed from the mailer and centrifuged. The eluate is collected into the leak-proof container. The centrifugation is accomplished in buckets which will hold either the mailers or the leak-proof containers. The sample remains in this container and aliquots are withdrawn for the various assays.

For HIV testing, the sample will be analyzed to determine the total concentration of IgG and/or IgA in the sample. If the sample contains more than a predetermined amount of IgG plus IgA, it will be deemed to be an "adequate sample" and will be tested for HIV serostatus. Data indicate that our pad actually collects more IgA than IgG, which is to be expected because IgA levels in oral fluid are known to be higher than those of IgG. For HIV testing, it is probable to use the LAV 1.0 or LAV 2.0 ELISA (Genetic Systems Laboratory) or the Organon Technika HIV ELISA. If the sample is reactive, the ELISA will be repeated. If it is repeatedly reactive, the sample will then be analyzed by a confirmatory assay, either Western Blot or IFA optimized for use with oral fluids.

Figure 1:
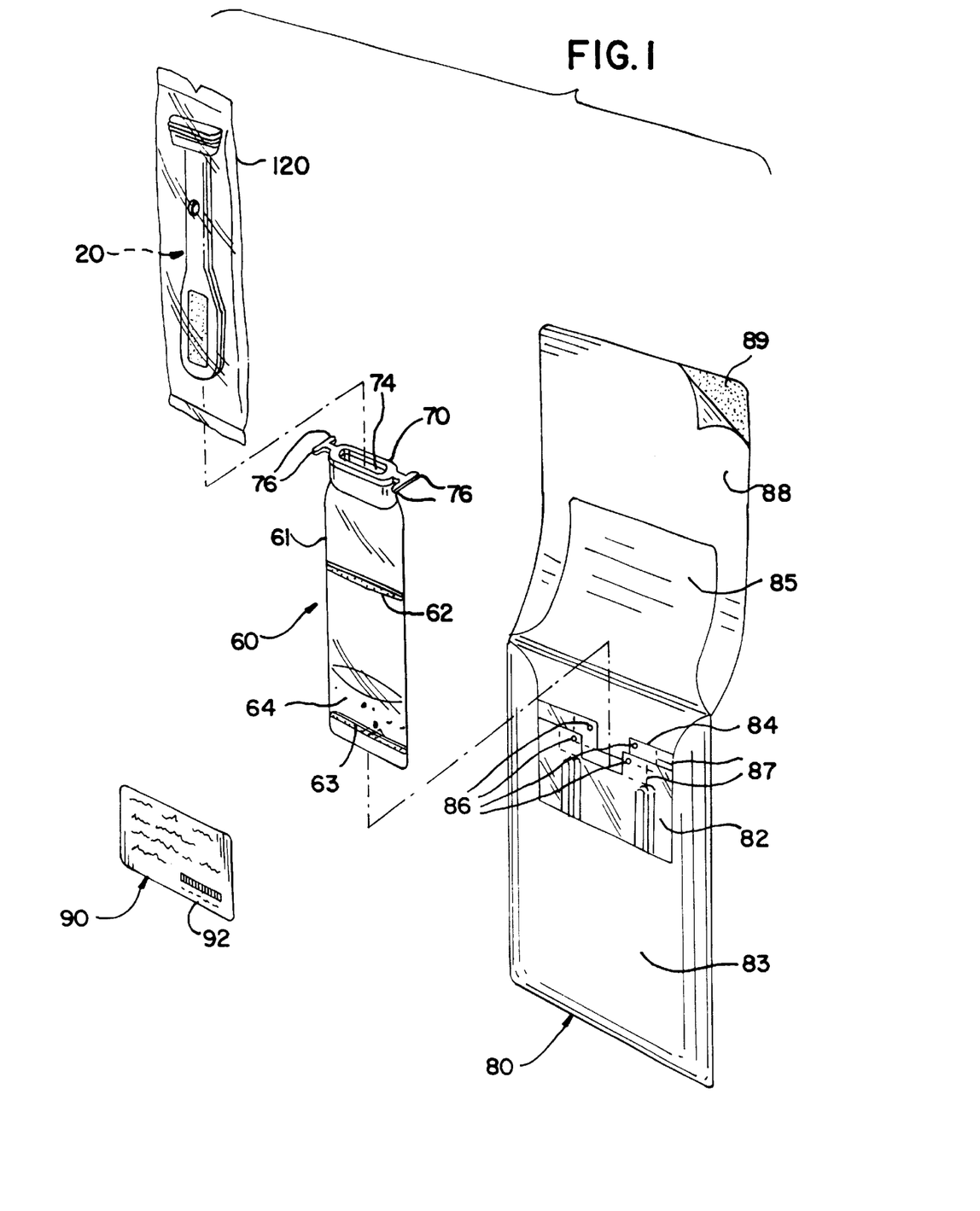
FIG. 1 is an exploded perspective view illustrating the components of the present invention.
Figure 2:
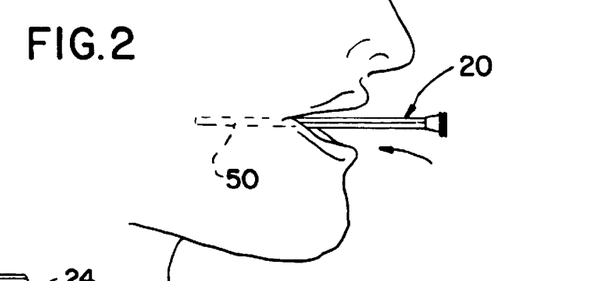
FIGS. 2, 3, 4 and 5 are schematic views showing the sequence of steps used to carry out the objectives of the present invention.

Illustrated in FIG. 1 are the various components used to collect an oral sample, seal and preserve such sample, and a means for protecting and mailing the oral sample to a reference laboratory for analysis. These components are inserted into a secondary package (not shown) which includes instructions for proper use.

Figure 8:
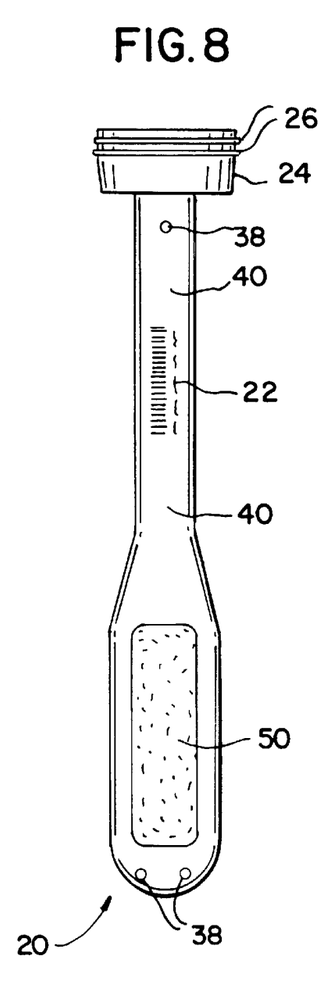
FIG. 8 is a rear view of the sample collection device.
Figure 9:
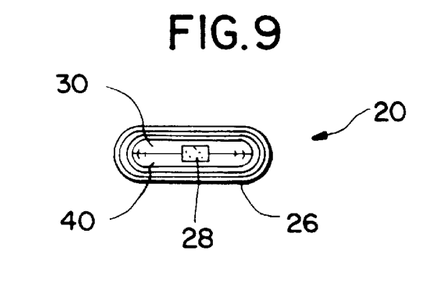
FIG. 9 is a distal end view of the sample collection device.
Figure 10:
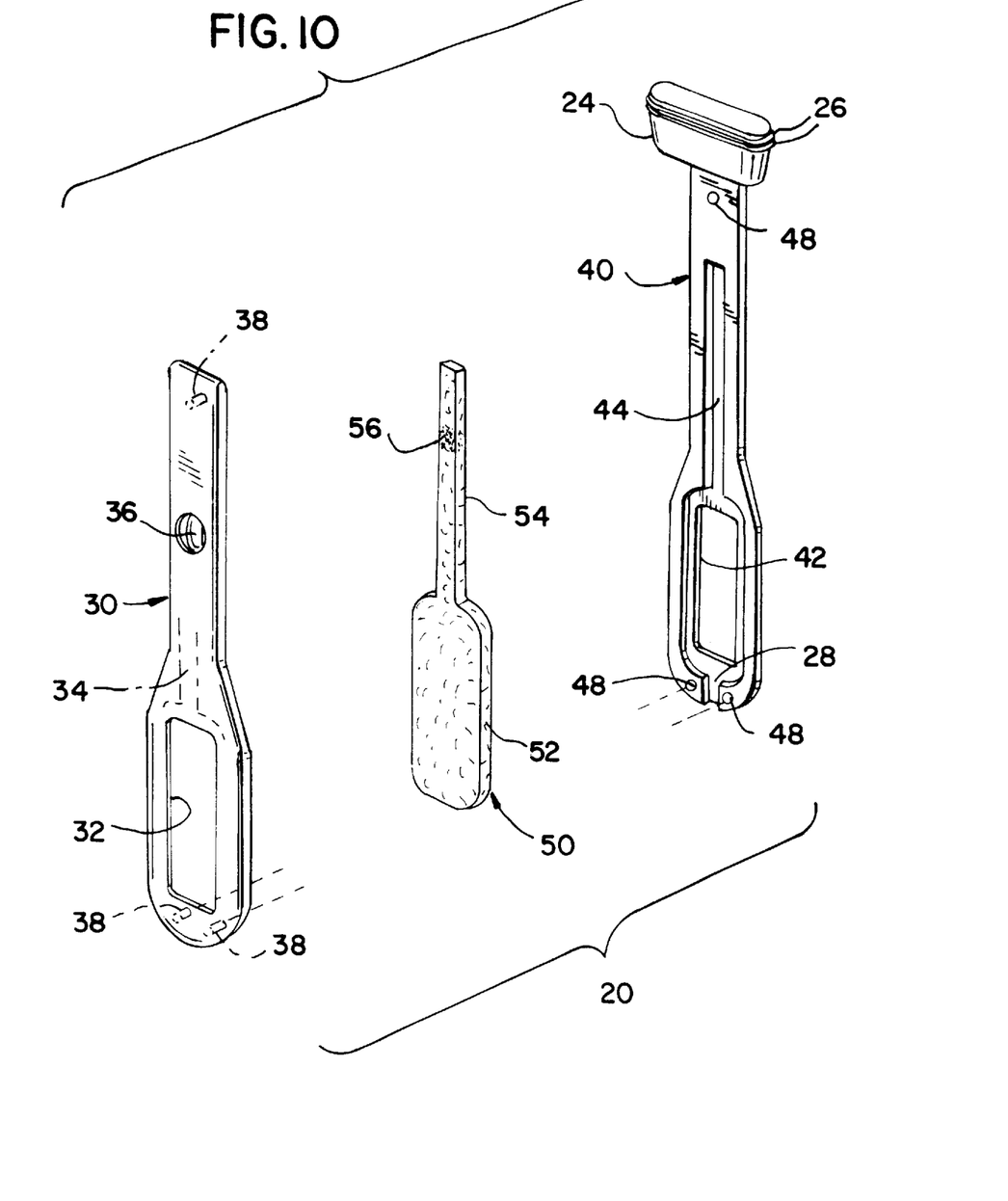
FIG. 10 is an exploded perspective view of the sample collection device.

With reference to FIGS. 1 through 5, the method of carrying out the present invention is shown. The consumer after having read the instructions, removes the sample collection device 20 from its sterile outerwrap 120. The user then places the sample collection device 20 in the mouth, comfortably in the mouth on the tongue ensuring that the pad is bathed in oral fluid. This allows the oral fluid sample in the user's mouth to be absorbed onto the sample collection device 20. Sample collection device 20 is at this point inserted into the preservative container 60, breaking first seal 62. Preservative held in space 61 soaks test pad 50. Sample collection device 20 is pressed into the top surface of preservative container 60, forming a watertight seal. The combination of sample collection device 20 and preservative container 60 is then disposed and snapped into the provided pre-paid mailer 80 and is sent to the laboratory. The fold over flap 200 (FIG. 15) may fold over device 20 placed in container 60. After waiting a predetermined amount of time, the user calls the toll-free telephone number on their identification card 90, giving the unique sample identification number 92 to accurately independently match with the identification number 22 on the sample collection device 20 (see FIG. 8) at the laboratory. The company then shares the test result with appropriate counseling.

FIGS. 6 through 10 illustrate sample collection device 20 in further detail. Sample collection device 20 is comprised of two flexible plastic handle halves 30 and 40 disposed on either side of pad 50.

Sample collection pad 50 is made of medical grade pure cotton and has a rectangular portion 52 and an upwardly extending portion 54. The oral sample initially makes contact with section 52 through openings 32 and 42 of handle halves 30 and 40, respectively. The sample then is absorbed through section 54 and makes contact with the color indicator 56, which can be (for example) yellow in color before testing, and changes color to (for example) red when a sufficient amount of sample has been obtained. This color change can be observed by viewing through aperture 36 in handle half 30. Sample collection pad is designed to hold between 0.75 ml and 1.0 ml of the oral fluid sample.

Handle halves 30 and 40 are joined by way of pins 38 on the inner surface of handle half 30 and receiving apertures 48 disposed on the inner surface of handle half 40. The means of securement-may be press-fit, adhesive, ultrasonic bonding or any other suitable means of attachment. Handle halves 30 and 40 have recesses 34 and 44 respectively formed on their inside surfaces to securely hold collection pad 50 when the assembly of the sample collection device 20 is completed.

Located at one end of sample collection device 20 is an enlarged hub portion 24. Hub portion 24 has disposed about its periphery a pair of outwardly extending ridges 26 which are configured to sealingly mate (sometimes called the third seal) with the collar of the preservative container 60, which will be discussed in greater detail below. Located at the other end of sample collection device 20 is an opening 28. Opening 28 allows the oral fluid sample to be extracted during the centrifuge process at the laboratory. Positioned on the outside of handle half 40 is unique identification means 22. This identification means 22 matches identification means 92 on user's card 90.

Figure 11:
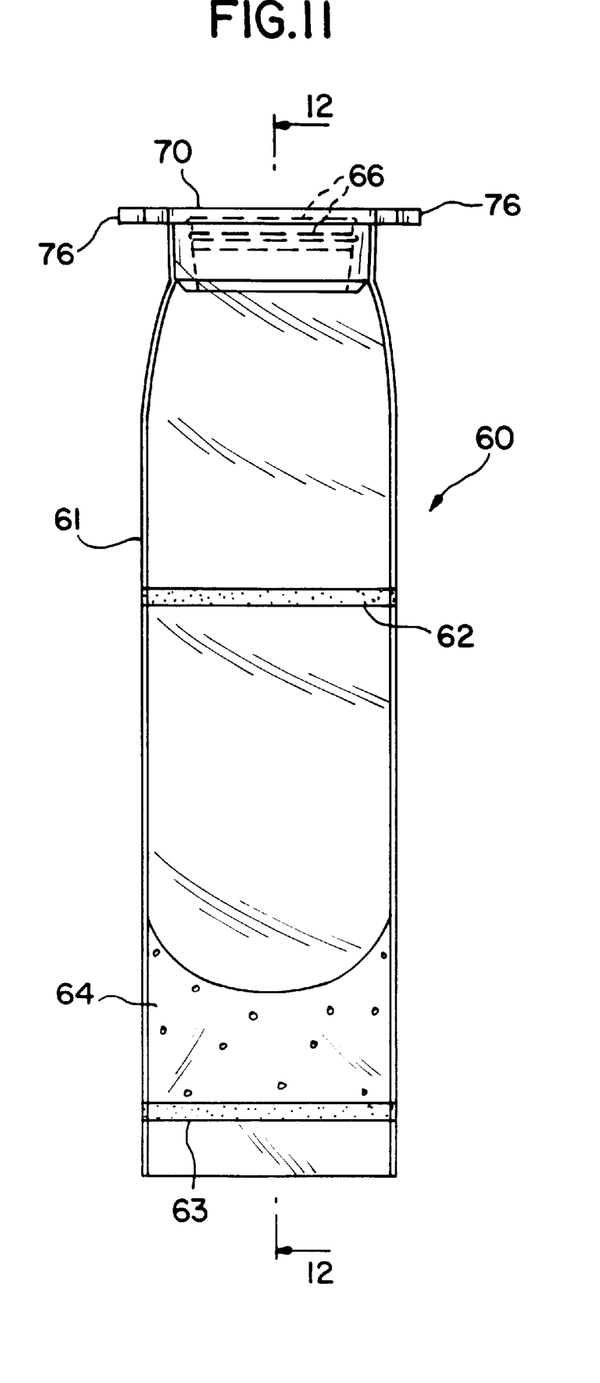
FIG. 11 is a front view of the preservative container.
Figure 12:
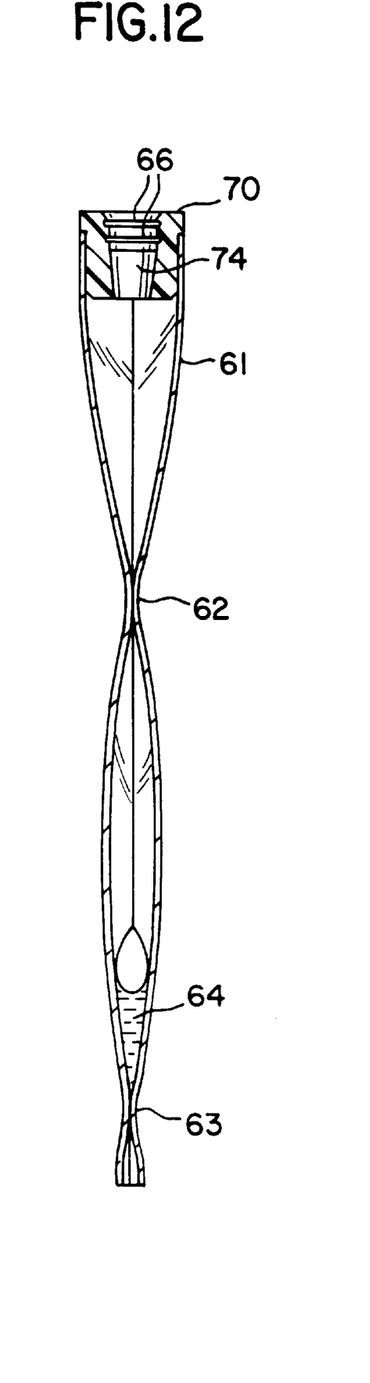
FIG. 12 is a cross-sectional view of the preservative container.
Figure 13:
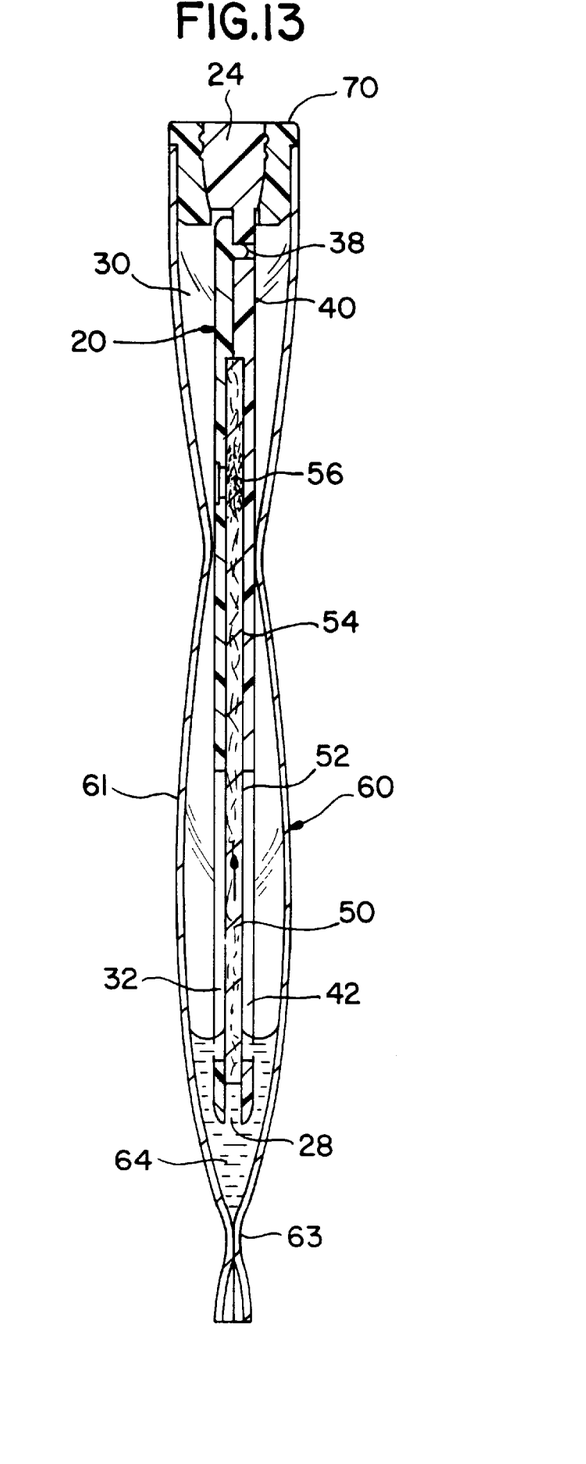
FIG. 13 is a cross-sectional view of the sample collection device sealed within the preservative container as taken along cross-section line 13—13 of FIG. 11.

Now referring to FIGS. 11, 12 and 13, the preservative container 60 is formed by joining an open ended, flexible, impermeable plastic pouch 61 to a plastic collar 70. This can be done by heat sealing adhesives and the like. A bottom (sometimes called second) seal 63 is formed, preservative liquid 64 is added to the pouch 61 and then (sometimes called first) temporary seal 62 is formed.

This arrangement keeps the user from coming into contact with the preservative liquid, and prevents any spillage during shipment of test kits to retail outlets. Ultimately, as previously discussed, the user breaks through seal 62 with the sample collection device 20. Then, at the laboratory, the bottom seal 63 will open during the centrifuge process. It should be noted that bottom seal 63 may be curved in shape, to allow adequate coverage of preservative on collection device 20. The collar 70 has a central open portion 74 to receive hub 24 of sample collection device 20. Located on the inner surface of opening 74 as a pair of grooves 66 which form annular recesses to receive the ridges 26 of hub 24, as best seen in FIG. 13. This forms a watertight (third) seal so that the sample collection device 20 is secure during shipment to the laboratory.

Figures 3, 4, 5:
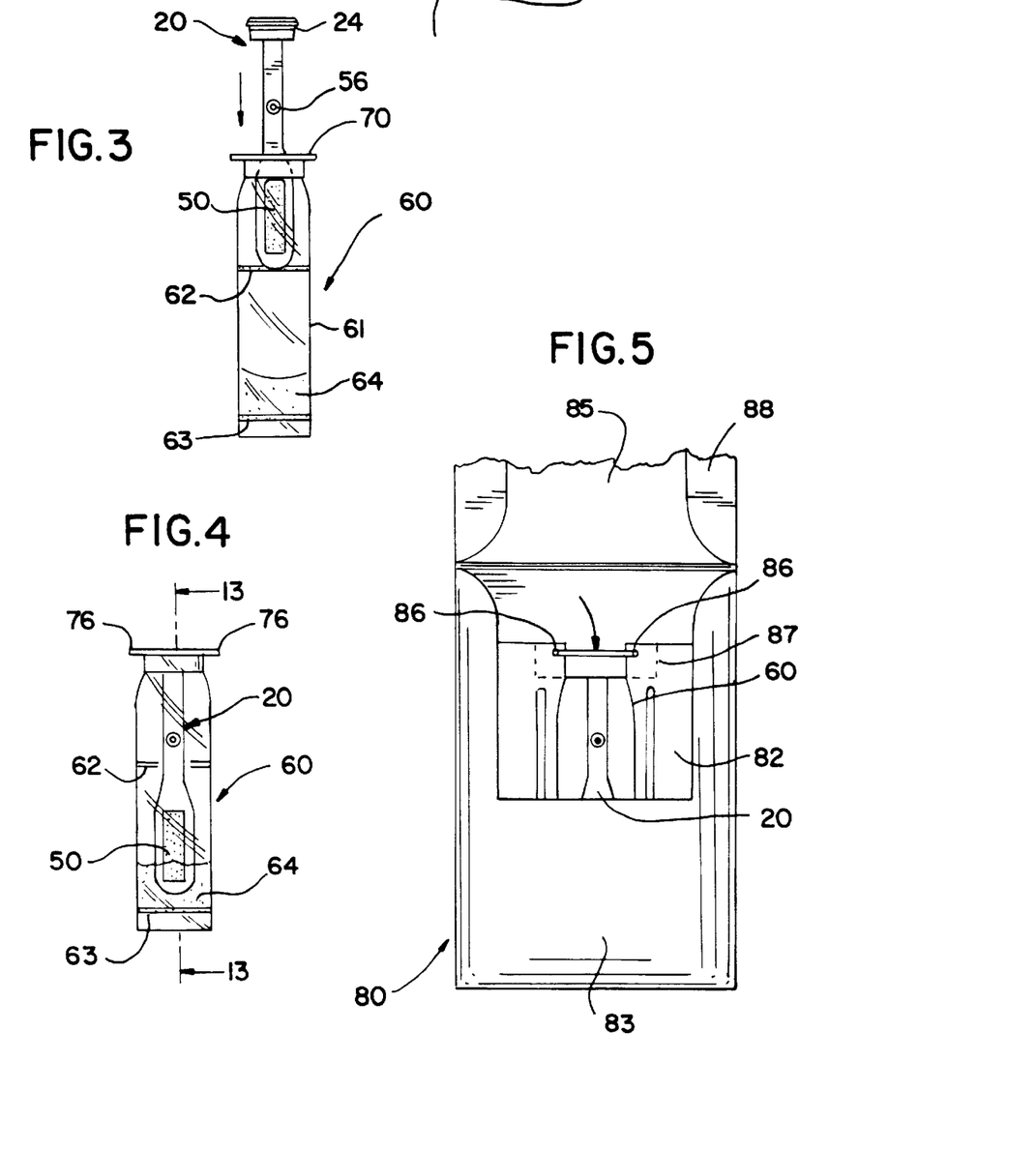
Figure 6:
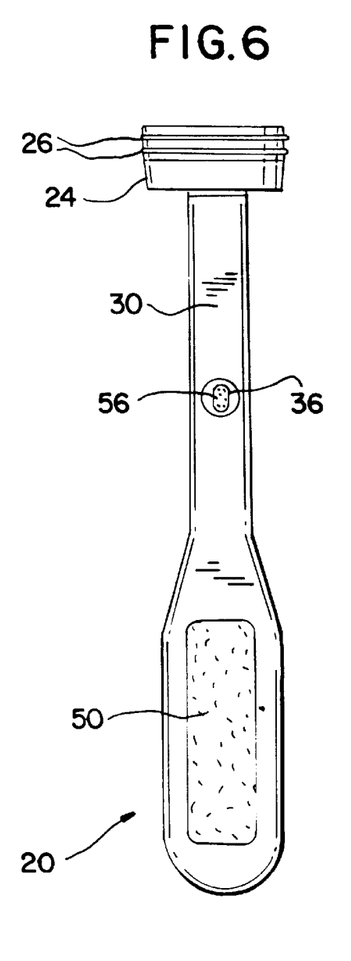
FIG. 6 is a front view of the sample collection device.
Figure 7:
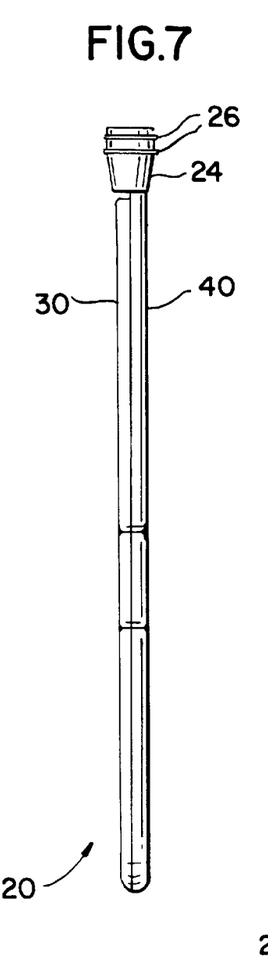
FIG. 7 is a side view of the sample collection device.

Referring now back to FIGS. 1 and 5, positioned on either side of collar 70 are two pairs of projection posts 76. These posts 76 mate with openings 86 in the mailer 80. The user inserts the combined sample collection device 20 and preservative container 60 into and between protective panels 82 and 84 of mailer 80. Once fully inserted, the posts 76 and openings 86 become engaged. The user then simply removes adhesive release liner 88 from adhesive 89, located on cover flap 85, and presses cover flap 85 onto primary portion 83, and the mailer is then ready for shipment.

Optional perforations in panels 82 and 84 allow for easy detachment and removal of the combined sample collection device 20 and preservative container 60 by the laboratory for testing.

Figure 14:
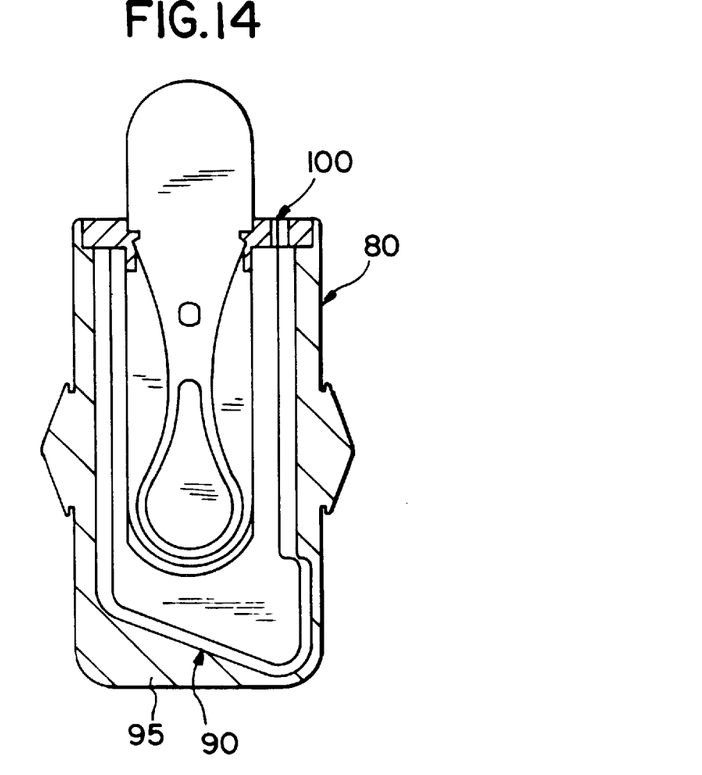
FIG. 14 is a schematic illustration of the mailer pouch with cuvette.
Figure 15:
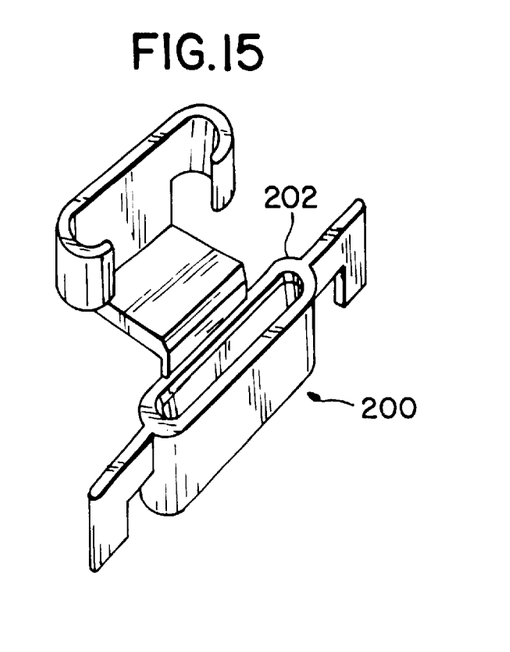
FIG. 15 is a perspective view of a lock on the mailer pouch useful to hold the preservative pouch therein.

As seen from FIGS. 14 and 15, certain alternate embodiments of aspects of the present invention are also disclosed. The flexible collection pouch and reagent strip are similar in the description of FIG. 14. However, now there is a tube or cuvette 100 provided in the mailer 80 which allows the user to extract sample after centrifugation. Thus, the eluate collects at the base of the mailing pouch 80 and this is thereafter able to have sample removed through the cuvette 100. A portion 95 of the mailing pouch 80 can be separated for centrifugation. This portion 95 of the mailing pouch 80 contains the cuvette 100 and protective covering 102 for the flexible pouch and as well, contains the flexible pouch and the reagent strip. The assembly 95 is centrifuged in a special adapter built into the centrifuge. The eluate collects at the bottom of the cuvette 100 and is then able to be removed and analyzed. The cuvette 100, of course, contains the same identifying markings as on the mailing pouch 80, the reagent pad 20 and the flexible preservative pouch 60.

As seen in FIG. 15, there is also described a fold-over flap 200 which is adaptable to seal the flexible pouch 60 with the reagent pad 20. The fold-over flap 200 is contained on top of the flexible preservative pouch 60 and has a collar 202 which protects the flap 200 so that the reagent strip or pad 20 cannot be "backed out" of the flexible pouch 60. In this fashion, the only way the pad 20 can be removed is by breaking the portion 95 from the other 105 portions so that it can be taken out of the device with the flexible preservative pouch 60 intact.

Figure 16:
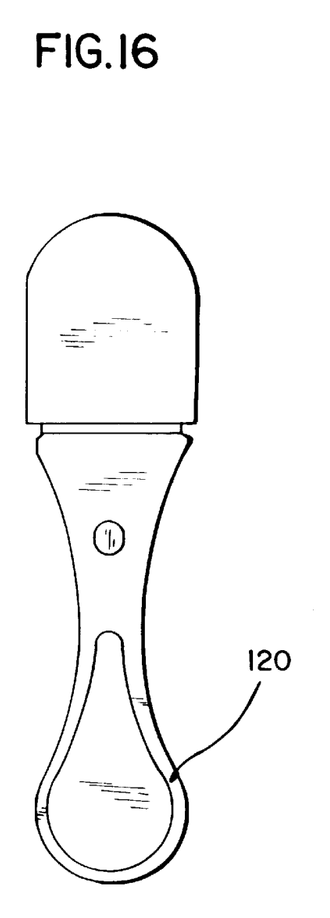
FIGS. 16, 17 and 18 are views of a second embodiment of an oral collection strip.
Figure 17:
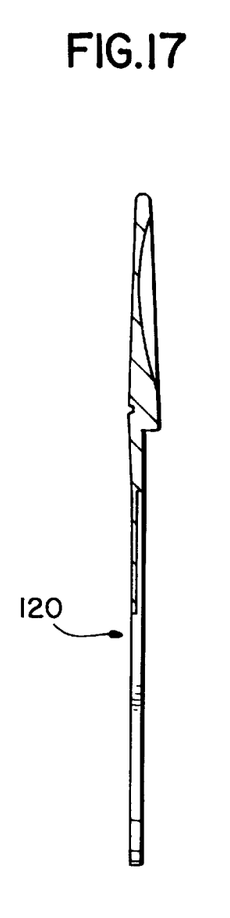
Figure 18:
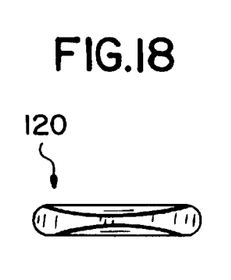

As seen in FIGS. 16, 17 and 18, a proposed alternate collection pad 120 is provided; while ergonomically more pleasing, it nevertheless provides all the functional capability of collection pad 20.

In summary, the proposed new product provides the ability to obtain and mail a fluid sample to a reference laboratory for analysis, for instance for HIV antibody testing. The main advantages of this product are that it is:

Safe and easy to use.

A simple indicator showing when sufficient sample has been collected is provided for the user.

A preservative is provided which will ensure the sample survives until it reaches the laboratory for analysis.

The flexible collection device and pouch containing the preservative are designed so that the return mailer will pass through automated mail sorting equipment, and so will be able to be returned to the lab at the fist class letter rate, hence reducing costs.

The pouch is designed with a series of temporary seals. The distal lowest seal is designed to break during centrifugation. In this way, the mixture of sample and preservative is easily extracted from the reagent pad and is used as the sample for the analysis.

The pouch is contained within a leak-proof container within the mailer. The whole mailer can be either centrifuged "as is", or opened and just the plastic insert centrifuged. In either case, the leak-proof container receives the eluate during centrifugation and also is the storage vessel for the sample during analysis.

The results will be forwarded from the reference lab to the testing service when the user calls, gives his/her unique sample identification number and is given the result of the testing, with appropriate counseling.

It should be noted that although certain designs for the present invention have been set forth, a variety of different designs and materials could be used without affecting the spirit and scope of the present invention.

What is claimed is:

1. A flat pouch for holding a regent strip said pouch having proximal and distal ends and said reagent strip having a flat configuration with a pad sized to fit on the tongue to sample oral fluid, said pouch comprising:

a chamber and a first seal at said proximal pouch end on said pouch and a second seal distal to said first seal;

said second seal stronger than said first seal; and further comprising a collar capable of forming a third seal proximal to said first seal.

2. The pouch of claim 1 combined with a reagent pad, said reagent pad capable of breaking said first seal.

3. The combination of claim 2 wherein said reagent pad has a seal which mates with said collar.

4. A flat pouch for holding a reagent strip said pouch having proximal and distal ends and said reagent strip having a flat configuration with a pad sized to fit on the tongue to sample oral fluid, said pouch comprising:

a chamber and a first seal at said pouch proximal end and a second seal distal said first seal: and sad second seal stronger than said first seal;

and further comprising a collar capable of forming a third seal proximal to said first seal.

5. In combination:

a reagent pad and a reagent strip having a flat configuration with a pad sized to fit on the tongue to sample oral fluid; and a chamber and a pouch with proximal and distal ends having a first seal at said pouch proximal end and a second seal distal said first seal; and said second seal stronger than said first seal, and further comprising a collar capable of having a third seal proximal to said first seal, wherein said pad is insertable into said pouch by breaking said first seal.

6. The combination of claim 5 wherein said pad has a seal which mates with said collar.

7. The combination of claim 5 further comprising a preservative in said chamber.

8. In combination:

a reagent pad and a reagent strip having a flat configuration with said pad sized to fit on the tongue to sample oral fluid; and a chamber and a pouch with proximal and distal ends and a first seal at said proximal end and a second seal distal said first seal.

9. The pouch of claim 8 further comprising a collar capable of forming a third seal proximal to said first seal.

10. The pouch of claim 9 wherein said reagent pad a capable of breaking said first seal.

11. The combination of claim 10 wherein said reagent pad has a seal which mates with said collar.

12. The pouch of claim 8 wherein said reagent pad is capable of breaking said first seal.

13. The combination of claim 8 further comprising a preservative in said chamber.

14. A flat pouch for holding a reagent strip said pouch having proximal and distal ends, and said reagent strip having a flat configuration with a pad sized to fit on the tongue to sample oral fluid, said pouch comprising:

a chamber and a first seal at said pouch proximal end and a second seal distal said first seal; and further comprising a collar capable of forming a third seal proximal to said first seal.

\* \* \* \* \*